(12) United States Patent
Johnson et al.

(10) Patent No.: US 8,027,849 B2
(45) Date of Patent: Sep. 27, 2011

(54) SYSTEM AND METHOD TO SCHEDULE RESOURCES IN DELIVERY OF HEALTHCARE TO A PATIENT

(75) Inventors: Christopher Johnson, Clifton Park, NY (US); Kunter Akbay, Niskayuna, NY (US); Jenny M. Weisenberg, Niskayuna, NY (US); Paul Cuddihy, Ballston Lake, NY (US); Onur Dulgeroglu, Niskayuna, NY (US); David Toledano, Round Lake, NY (US)

(73) Assignee: General Electric Company, Schenectady, NY (US)

( * ) Notice: Subject to any disclaimer, the term of this patent is extended or adjusted under 35 U.S.C. 154(b) by 403 days.

(21) Appl. No.: 12/239,209

(22) Filed: Sep. 26, 2008

(65) Prior Publication Data

US 2009/0089092 A1 Apr. 2, 2009

Related U.S. Application Data

(60) Provisional application No. 60/976,582, filed on Oct. 1, 2007.

(51) Int. Cl.
G06Q 10/00 (2006.01)
G06Q 50/00 (2006.01)

(52) U.S. Cl. .......................................................... 705/2
(58) Field of Classification Search .................. 705/2, 3, 705/8; 206/373
See application file for complete search history.

(56) References Cited

U.S. PATENT DOCUMENTS

| | | | | |
|---|---|---|---|---|
| 2007/0136118 A1* | 6/2007 | Gerlach et al. | ..................... | 705/8 |
| 2007/0214013 A1* | 9/2007 | Silverman | ......................... | 705/2 |
| 2008/0312959 A1* | 12/2008 | Rose et al. | ......................... | 705/2 |
| 2009/0071854 A1* | 3/2009 | Martin | ......................... | 206/373 |

* cited by examiner

Primary Examiner — Gerald J. O'Connor
Assistant Examiner — John Pauls
(74) Attorney, Agent, or Firm — Fletcher Yoder P.C.

(57) ABSTRACT

A method to schedule resources in delivery of healthcare to a series of patients is provided. The method comprises the steps of identifying an availability of the series of resources to deliver the healthcare to each patient; calculating a predicted duration to deliver the healthcare to each patient; calculating a schedule including a block of time dependent on the predicted duration for each resource to deliver healthcare to the patient, the block of time including a start time and an end time; calculating a confidence level in the schedule, the confidence level including a probability that one or more of the resources will not be available for the block of time of the schedule or calculating a likelihood that one or more resources will be available for the block of time in the schedule; and outputting the schedule and the confidence level in the schedule for display.

18 Claims, 8 Drawing Sheets

US 8,027,849 B2

SYSTEM AND METHOD TO SCHEDULE RESOURCES IN DELIVERY OF HEALTHCARE TO A PATIENT

CROSS REFERENCE TO RELATED APPLICATIONS

This application is related and claims benefit of priority to Provisional Application No. 60/976,582 entitled "METHOD TO VIEW BIOMETRICAL INFORMATION AND DYNAMICALLY ADAPT SCHEDULE AND PROCESS INTERDEPENDENCIES WITH CLINICAL PROCESS DECISIONING", filed Oct. 1, 2007; and to U.S. application Ser. No. 12/040,668 entitled "SYSTEMS AND METHODS FOR VIEWING BIOMETRICAL INFORMATION AND DYNAMICALLY ADAPTING SCHEDULE AND PROCESS INTERDEPENDENCIES WITH CLINICAL PROCESS DECISIONING", filed Feb. 29, 2008, and both are hereby incorporated herein by reference in there entirety.

BACKGROUND

The subject matter relates generally to business process management systems, and more particularly to scheduling systems in the clinical setting, such as healthcare delivery institutions or hospitals.

Healthcare delivery institutions are business systems that can be designed and operated to achieve their stated missions robustly. As is the case with other business systems such as those designed to provide services and manufactured goods, there are benefits to managing variation such that the stakeholders within these business systems can focus more fully on the value added core processes that achieve the stated mission and less on activity responding to variations such as delays, accelerations, backups, underutilized assets, unplanned overtime by staff and stock outs of material, equipment, people and space that is impacted during the course of delivering healthcare. Additionally, as the need arises for procedures and interventions where time is of the essence (which is very often in healthcare and other service delivery business systems), the capacity to have rapid and well-orchestrated responses without sacrificing other performance aspects of the enterprise is highly desired.

BRIEF SUMMARY

The system and method described herein can be operable to adapt the scheduling of clinical activities and procedures in real time that incorporate variation, asset readiness, biometrical changes in the state of patient health, changes in process necessitated by protocols which must be executed that are different than what was originally scheduled, staff and equipment preferences, interdependencies and information flow into the clinical delivery of healthcare that can enable "what-if" capability for prospective decision support given the changes that are occurring and provide viable ways forward that minimize the overall negative system impacts.

The subject described herein includes an embodiment of a method to schedule a plurality of resources in delivery of healthcare to a series of patients. The method comprises the steps of identifying an availability of the series of resources to deliver the healthcare to each of the series of patients; calculating a predicted duration to deliver the healthcare to each of the patients; calculating a schedule including at least one block of time dependent on the predicted duration for each the series of resources to deliver healthcare to one or more of the patients, the at least one block of time including a start time and an end time; calculating a confidence level in the schedule, the confidence level including at least one of a probability that one or more of the resources will not be available for the at least one block of time of the schedule, or calculating a likelihood that one or more resources will be available for at least one block of time in the schedule; and outputting the schedule and the confidence level in the schedule for illustration in a display.

The subject described herein also includes an embodiment of an article of manufacture in combination with a plurality of resources in delivering healthcare to a plurality of patients. The article of manufacture comprises at least one computer-readable medium; and a plurality of computer readable instructions stored on the at least one machine readable medium, the plurality of computer readable instructions representative of the steps of identifying an availability of the plurality of resources to deliver the healthcare to each of the plurality of patients, calculating a predicted duration to deliver the healthcare to each of the patients calculating a schedule including at least one block of time dependent on the predicted duration for each the plurality of resources to deliver healthcare to one or more of the patients, the at least one block of time including a start time and an end time, calculating a confidence level in the schedule, the confidence level including at least one of a probability that one or more of the resources will not be available for the at least one block of time of the schedule, or calculating a likelihood that one or more resources will be available for at least one block of time in the schedule, and outputting the schedule and the confidence level in the schedule for illustration in a display.

DESCRIPTION OF THE DRAWINGS

These and other features, aspects and advantages of the present subject matter will become better understood when the following detailed description is read with reference to the accompanying drawings in which like characters represent like part throughout the drawings. The embodiments shown in the drawings are presented for purposes of illustration only. It should be understood, however, that the present subject matter is not limited to the arrangements and instrumentality shown in the attached drawings.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
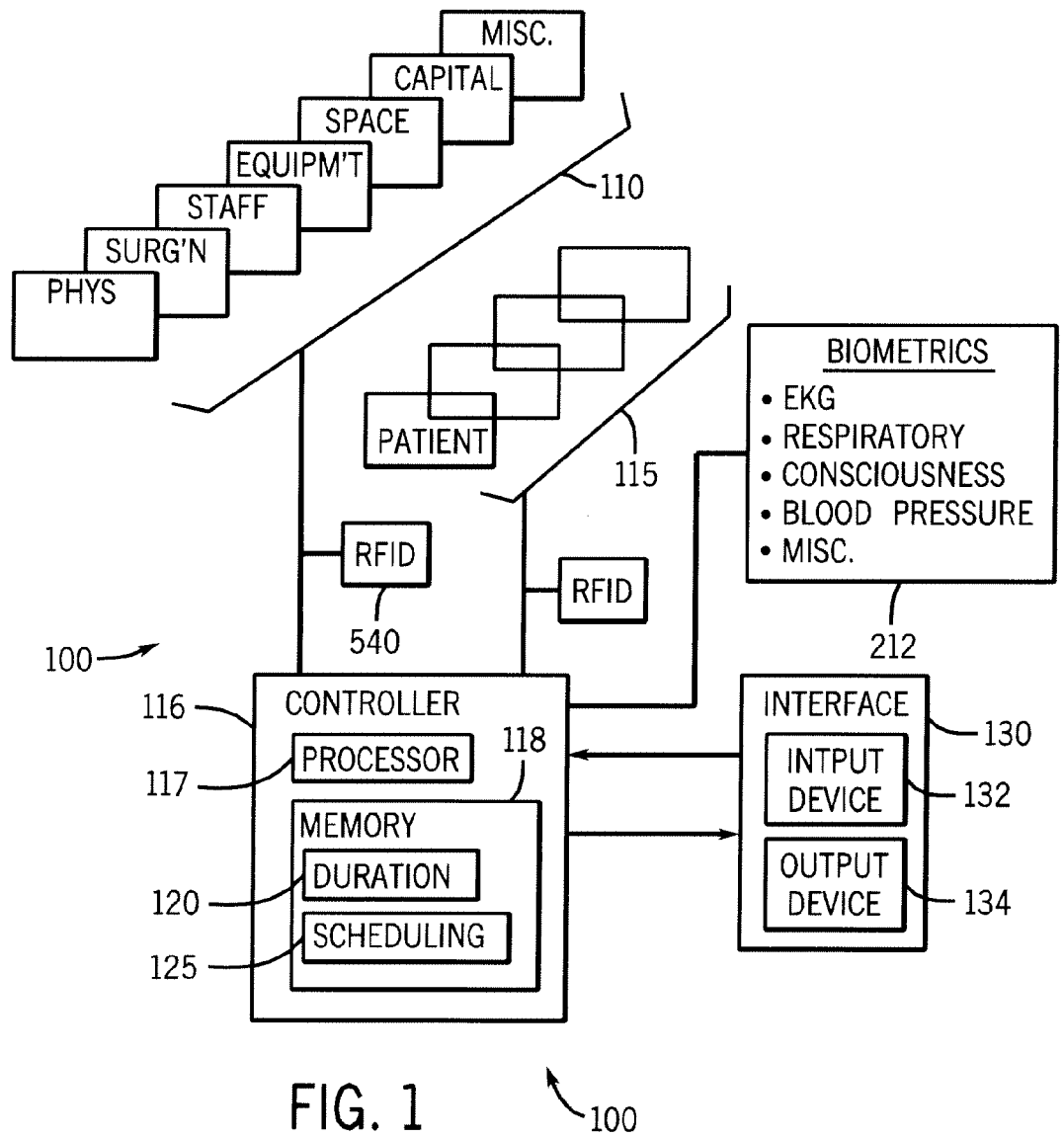
FIG. 1 is a schematic diagram that illustrates of an embodiment of a system to schedule resources in delivery of healthcare to a patient.

FIG. 1 illustrates an embodiment of a system 100 to schedule a series of resources 110 in delivery of healthcare to one or more patients 115. The system 100 can calculate a schedule of the resources 110 that is robust to unplanned events, can calculate a risk of the schedule of resources 110 to be performed as allotted or forecast, can illustrate simulations of scenarios that can affect the schedule of resources 110 beforehand, can calculate the schedule of resources 110 in a dynamic environment that will best achieve miscellaneous objectives, can acquire from or communicate data to the stakeholders (e.g., resources 110, patients 115, etc.) in the scheduling process, and can learn from what transpired so as to achieve departmental objectives.

An embodiment of the system 100 can generally create and output a proactive scheduling plan that includes calculating predictions or a forecast of procedure schedules and duration to avoid delays, and can cause an advanced warning with sufficient time to respond in an event that scheduled procedures will start or end before or after their scheduled time. The system 100 can also generate a recommendation regarding one or more specific decision(s) or action(s) that can be taken to add, drop or move specific cases of patients 115, or tasks of resources 110. The system 100 can also generally track or monitor availability of the resources 110 and available blocks of time in the schedule of the resources 110 associated with fluctuating demand and availability for the resources 110.

One embodiment of the system 100 includes controller 116 comprising at least one processor 117 in communication with at least one memory or computer storage medium 118 operable to store computer readable program instructions for execution by the at least one processor 117. An embodiment of the computer readable program instructions can be arranged in a duration predictor module 120; a scheduling module 125 configured to schedule procedures or activities in accordance with characterized times from the duration predictor module.

The system 100 can further include a user interface 130 operable to illustrate or visualize generated output received from the controller 116. The user interface 130 can include an input device 132 such as a keyboard, mouse, graphic link, control buttons, voice commands, toggle levers, touchscreens, etc. known in the art to receive data from an operator. The user interface 130 can further include an output device 134 such as a touch-screen, monitor, plasma monitor, liquid crystal monitor, LEDs, speaker, etc. known in the art to illustrate output to the operator of the system 100. The interface 130 can be configured to operate with and on mobile devices.

While embodiments are described with reference to delivery of healthcare (e.g., nursing home, ambulatory clinics, distributed care outside of the hospital, transport, etc.), the subject matter can be extended to other non-healthcare environments (e.g., industrial, commercial, etc.).

Medical procedures can include variation in duration of time to complete. When procedures take less than the forecast, valuable resources 105 can be underutilized and clinical flexibility can be degraded because the availability is unanticipated/unactionable. Variation in duration of time of procedures can also impact downstream processes, including patient handling, staffing, and equipment turn-around. When procedures take more time than forecasted, resources 110 may be unavailable for other procedures that were scheduled. Unavailability of one or more resources 110 can delay upstream processes, and create staffing shortfalls and increase fatigue stress to the stakeholders (e.g., resources 110 or patients 115).

An embodiment of the duration predictor module 120 is generally configured to characterize average duration times and variations from average duration times for a given procedure or activity. A technical effect of the duration predictor module 120 includes calculating a time interval to perform procedures. Activity data can be stored in order to create historical data (such as that visualized in histograms 305) such that the disclosed system 100 evolves or learns over time, as well as can improves accuracy of forecast durations and can increase a probability of achieving a schedule of tasks within a predetermined time and usage threshold.

Figure 2:
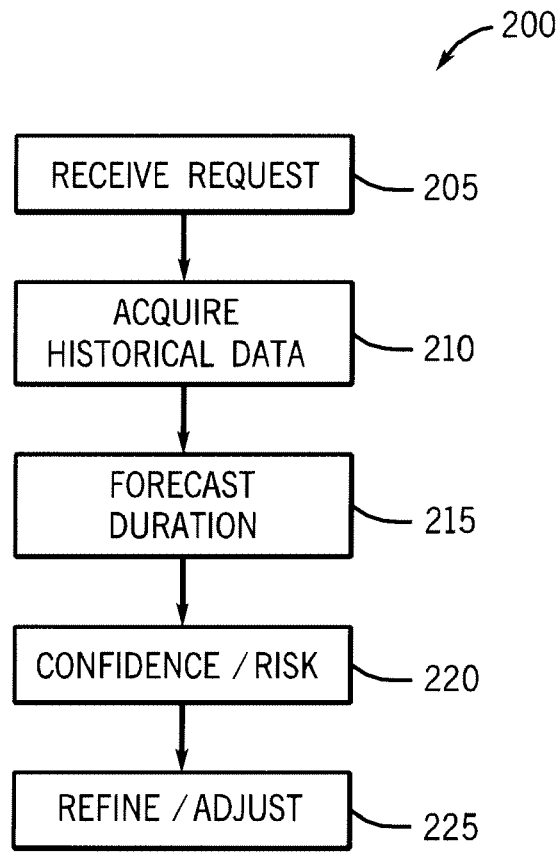
FIG. 2 is a schematic diagram that shows of an embodiment of a method to predict duration of a procedure to deliver healthcare to a patient.

FIG. 2 illustrates an embodiment of a method 200 to predict duration of a procedure to deliver healthcare to patients 115. Step 205 includes receiving or obtaining a request for delivery of a procedure to the admitted patient 115. Step 210 includes obtaining or receiving historical data of the resources 110 employed and historical duration of time tracked to complete the procedure. The historical data can be attributable to specific staff or other resources 110 employed in the performance of the procedure. The historical data can also be connected to biometric data 212 (e.g., weight, age, sex, blood pressure, respiratory rate, a measure of activity, chemical sensing, image-derived measures, etc.) of the patient 115 receiving the procedure, patient characterization compared to a peer group for the purposes of statistical forecasting, a patient's diagnosis related group (DRG), other ad hoc indicators which separately or jointly may be filtered and regression fitted to improve the forecast confidence interval, or combination thereof.

Step 215 includes calculating a predicted or forecast duration to complete the procedure on the admitted patient 115, so as to be assigned to or into blocks or slots of time in the schedule of resources 110 within available limits.

An example of calculating the forecast duration can include the following:

Forecast duration=Avg.duration*margin of safety*miscellaneous factor(s)

where the average duration includes average of historical durations of time to complete the procedure, wherein the margin of safety can be predetermined or received from the user, and wherein the miscellaneous factors to increase or reduce the forecast duration in view of tracked parameters can be dependent on parameters, including: variation of doctor/staff combinations in performance of the procedure; degree of severity of the patient's disease or medical condition; physical attributes of the patient 115 such as weight/height/body mass index (BMI)/surface area; availability of information, availability of resources 115; and occurrence of wrong or non-recorded information (e.g., time durations, multiple procedures conducted with only a subset being recorded, etc.).

A third embodiment of calculating step 215 can include calculating the median or mode of historical durations to complete the procedure in summation with a statistical variation (e.g., standard deviation) tracked by the system 100 in the calculating of the forecast duration. The calculating step 215 can include acquiring data of durations to complete procedures from peers (e.g., a consensus of professionals collated via industry working groups, societies and academic study, nursing, administrators, anesthesiologists or surgeons at similar and yet independent institutions). The calculating step 215 can include calculating or acquiring data of a mean and statistical variation of historical procedure duration vs. actual duration to completion for like cases through experiments on a subset population and/or procedure clustering for comparison to the historical record. The calculating step 215 can include acquiring or updating tracking data recorded duration to completion as procedures are completed that can be compared to forecast durations. The calculating step 215 can include calculating stochastic differential equations to dependent on one or of the above-described parameters that can affect the forecast duration so as add further robustness and adjustability to the output schedule of resources 110.

The history of procedural durations or time to completion can be collected or identified (e.g., per recognized procedural codes, per physician/surgeon/staff identification, etc.) and stored into a database or spreadsheet or analytical platform or repository. The calculating step 215 can include calculating a predicted variation (e.g., regression of above-described indicators or parameters against the historical duration times) that can then added to the forecast duration at the time of scheduling one or more resources 110 to a block of time in the delivery healthcare to the patients 115. The calculating step 215 can also include a combination of any of the portions of the embodiments described above.

Step 220 can include calculating a confidence or risk (e.g., probability or likelihood of variation to or lack of variation to) in one or more of the forecast duration or the overall allocation of forecast durations in the schedule of resources 110. An embodiment of step 220 can include generating or creating a probability density function (PDF) 305 (See FIG. 3) from the various embodiments of acquisition of data of durations of procedures or combinations thereof as described above in step 215.

Figure 3:
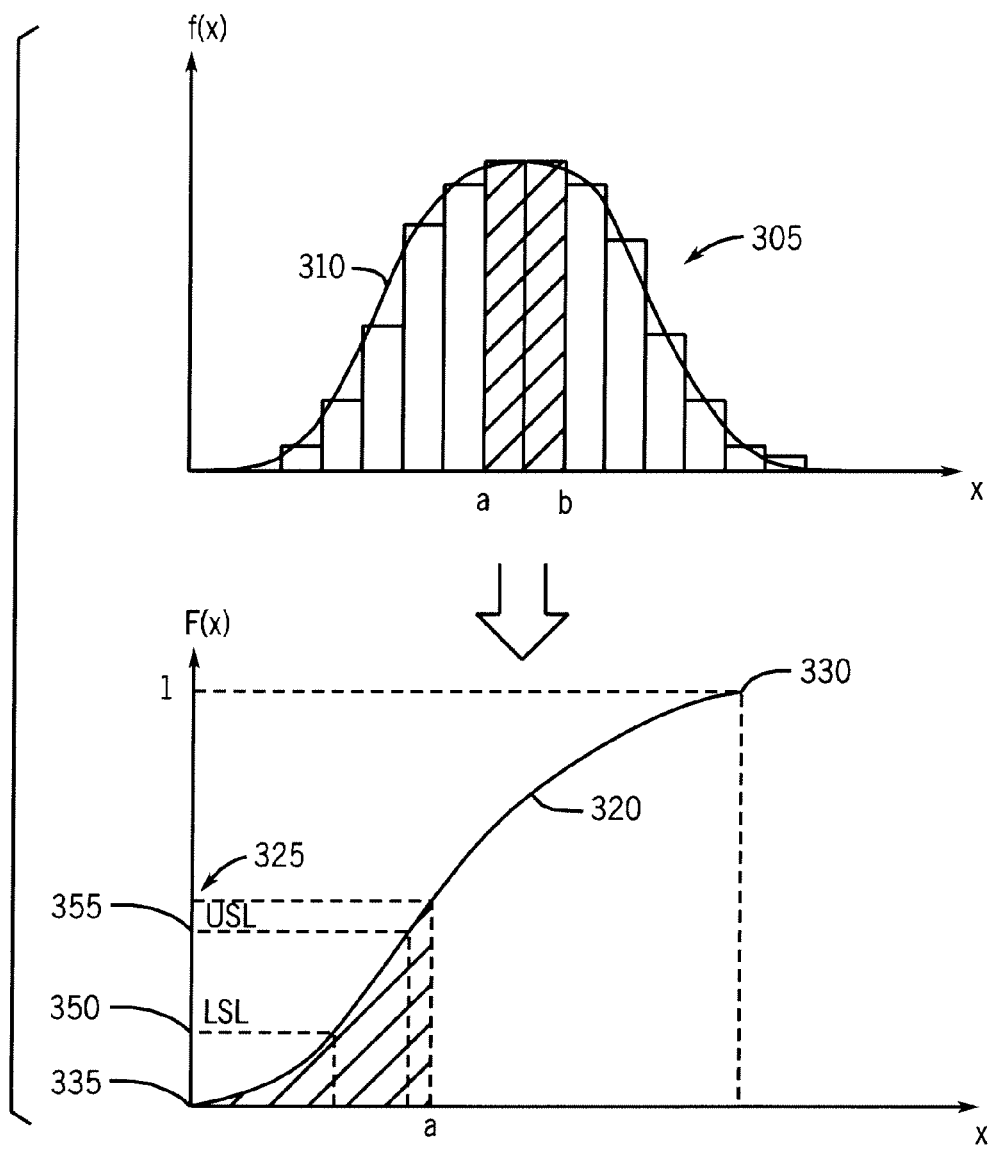
FIG. 3 is a schematic diagram that illustrates an embodiment of a method to calculate a confidence or risk in one or more of the forecast durations in the schedule of resources.

Referring to FIG. 3, an embodiment of step 220 can include arranging the acquired data of durations of procedures in a histogram format 305 or other statistical format that can be in combination with acquired data of parameters associated with variation in acquired data of historical durations. The system 100 (e.g., the scheduling module 125) can automatically normalize the histogram 305 of duration data. The step 220 can further include calculating a mathematical expression f(x) generally representative of the histogram in a continuous manner for variable (x) greater than zero, where the expression f(x) can represent the PDF 310 such that an integral of the expression f(x) between an interval [a,b] along the duration-axis (x) generally equates to a probability 315 of the forecast duration occurring between the interval [a,b].

The embodiment of the step 220 can also include calculating a cumulative probability density function (CPDF) 320 represented by the mathematical expression F(x) derived from the PDF 310 represented by the mathematical expression f(x) described above according to the relationship that f(x) generally equals the derivative of F(x) with respect to the forecast duration (x), such that the value of the cumulative probability density F(x) for a forecast duration value [a] generally represents a probability 325 of the forecast duration being less than the value [a].

For example, a forecast duration that correlates to a one hundred percent probability 330 according to the CPDF 320 has the maximum chance of matching the actual duration of the procedure being completed within a threshold relative to the forecast time interval. In a similar manner, a value of forecast duration that correlates to zero percent probability 335 generally represents the lowest chance of matching the actual duration of the procedure. One embodiment of risk that a procedure will not end with a threshold variation (e.g., five minutes, fifteen minutes, one-hour, or any interval time) of the forecast duration can be described as generally an inverse to the probability that the procedure ends within the threshold variation of the forecast duration, such that a one-hundred percent risk generally correlates to a zero percent probability 335 as defined by the CPDF 320, and a zero percent risk generally correlates to a one-hundred percent probability 330 as by the CPDF 320. Another embodiment of risk can be defined to be synonymous with probability that procedure will end within threshold variation of the forecast duration.

According to one embodiment, the system 100 generally calculates the forecast duration that generally correlates to an predicted value of duration with generally a fifty percent probability or likelihood of equaling or being less than the actual duration of the procedure, or can be generally defined where there is a fifty percent likelihood that the procedure will not take longer than the forecast duration, as defined by the mathematical expressions for the PDF 310 or CPDF 320. The system 100 can calculate the zero probability forecast duration and the maximum probability forecast duration in direct relation to a probability zero point and relative to the one hundred percent probability, respectively, as calculated from the CPDF 320.

An embodiment of step 215 can include calculating the forecast duration within or dependent on a received or predetermined confidence or probability as calculated in accordance to the expressions f(x) and F(x) of the PDF or CPDF, respectively, where (x) represents the duration to completion of a procedure. In response to having a predetermined or acquired general value or range of confidence or risk, the step 215 can include calculating the forecast duration that mathematically depends on or correlates to the general value or range of confidence or risk according to the mathematical expressions for the PDF 310 and CPDF 320 as represented by f(x) and F(x), respectively, as described above. The forecast duration can depend on the acquired confidence or risk can include addition of the margin of safety or other variation as described above.

The step 215 can include receiving an input of an initial likelihood of availability or reliability or an initial risk of unavailability, and calculating an update or change to likelihood of availability or reliability or risk of unavailability dependent on actual or historical data. The system can also receive input or updates to values of the above-described probabilities of availability or risk of unavailability from a remote provider or a peer group of independent institutions that may not otherwise be in shared communication of this information with one another.

An embodiment of step 215 can include expressing the schedule risk as the schedule of resources 110 to deliver healthcare procedures to the series of patients 115 that can be completed by 7 PM with ninety percent confidence or probability of completion either within an acceptable threshold range (an explicit parameter setting defining an acceptable duration) or no variation. The system 100 can calculate the value of forecast duration correlated to ninety percent confidence as defined by the CPDF. A back propagation to the discrete cases can be executed such that the individual error terms (variation) in the forecast duration can be incorporated to the calculation of the schedule of resources 110 in fractional steps until such time as the portfolio of procedures or caseloads can meet throughput or risk thresholds.

The system 100 can calculate or receive instructions of a lower specification limit (LSL) 350 and upper specification limit (USL) 355 of probability or schedule risk. According to one embodiment, the LSL can generally represent a minimum probability threshold (the most schedule risk) of completing the procedure within the forecast duration. The USL can generally represent a "cushion" or "margin" such as generally represented as an adjustable surplus probability in excess of an expected duration probability. The LSL and USL can be predetermined, or adjustable parameters (e.g., a sliding graphic scale, a data entry graphic via the interface, a scroll-down menu, etc.) and can be represented as logical rules in a decision support in generating the schedule of resources 110.

For example, the system 100 can automatically calculate versions of the schedule of the resources to complete with "50% probability", "80% probability", "95% probability", respectively, and/or any other desired likelihood or risk.

The acquisition of historical data may be sufficient to distinguish between forecast durations of procedures with statistical significance, and the step 220 can include partitioning of the histogram 305 of durations of at least a portion of procedures into clusters such that each cluster is associated with the PDF of the forecast time duration. The summation of the PDFs of the clusters can form the general enumeration of the historical procedures, less known data defects or special events or observations.

Step 225 can include receiving or measuring actual attributes and procedure times and executing techniques (e.g., artificial neural networks, multivariate regression, analysis of variance (ANOVA), correlation analysis, etc.) to refine or adjust the calculation of the forecast durations and tighten the bounds or range of confidence or risk in those forecast durations.

An embodiment of the scheduling module 125 can generally include a planning module operable to allocate or reserve resources 110 independently or within a block to schedule the resources 110 or patients 115 for a desired time period (e.g., minutes, hourly, daily, monthly, etc.). The scheduling module 125 can also be operable to re-sort the time slots in the schedule of the resources 110 in such a way as to satisfy constraints and departmental objectives, given preferences and availabilities. For example, the embodiment of the scheduling module 125 can schedule or reserve time to a space (e.g., rooms) to perform a variety of procedures on patients 115, to enhance objectives (e.g., case mix, staff satisfaction, safety, etc.). The scheduling module 125 can acquire preferences of the stakeholders (e.g., resources 110 such as surgeon, physician, nurse, technician, anesthetist, operating room, medical equipment, or patients 115). Preferences and departmental objectives may be traded off in the scheduling sort/optimization according to heuristics, penalty functions or math programming techniques familiar to those skilled in operations research.

Figure 4:
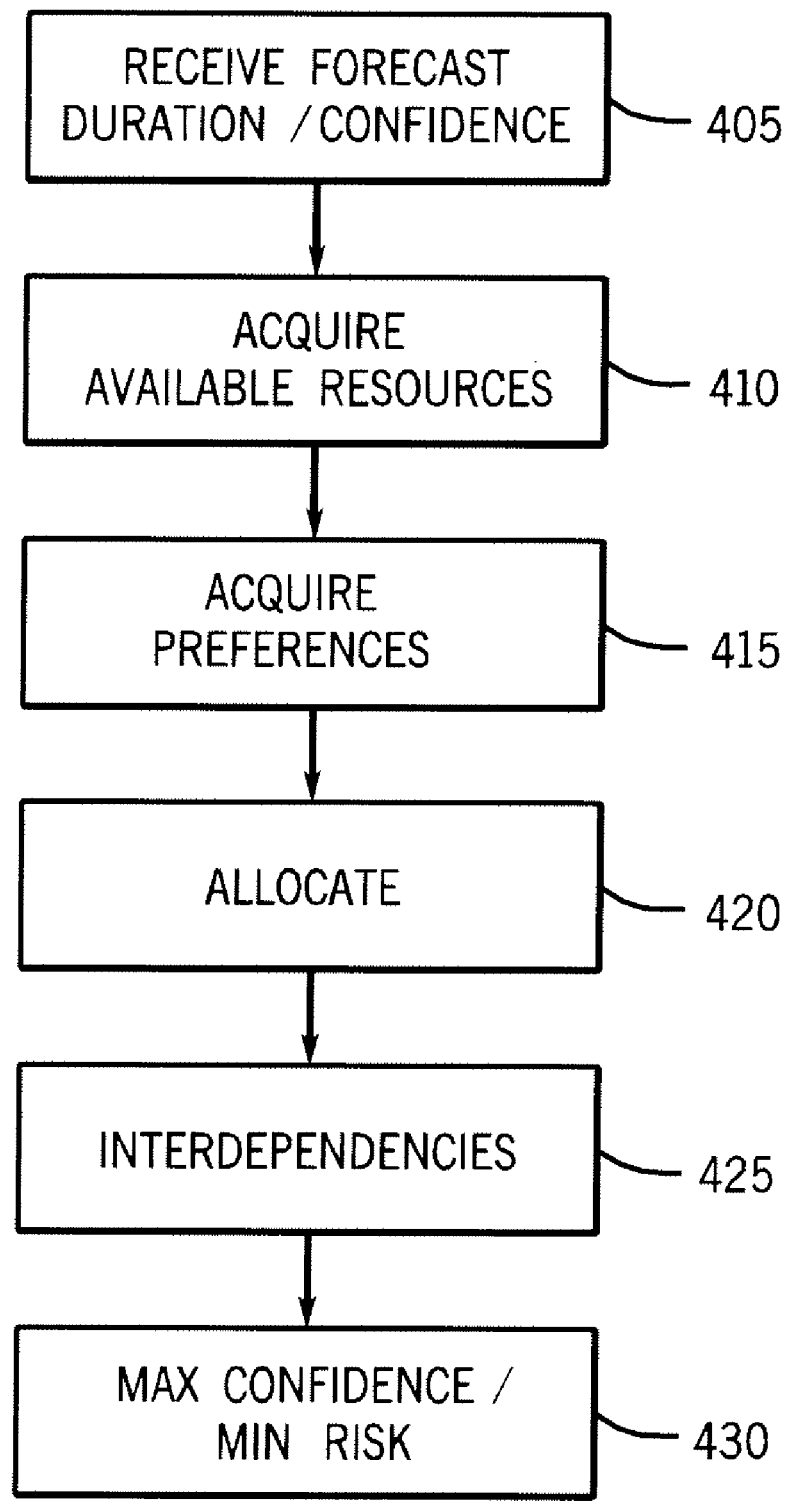
FIG. 4 is a schematic diagram illustrative of an embodiment of a method to schedule resources in a delivery of healthcare to patients.

FIG. 4 illustrate an embodiment of a method 400 generally representative of multiple program instructions of the scheduling module 125 for execution by the processor(s) of the system 100 in managing scheduling of resources 110. Step 405 can include receiving forecast duration or confidence/risk of procedures to deliver healthcare to patients 115. Assume for sake of example that the schedule of an occupation or use of resources 110 (e.g., rooms, staff, and equipment) to deliver healthcare to the patients 115 comprises a series of blocks or slots of time (e.g., hours, minutes, etc.) of various forecast duration. Step 410 can include acquiring identification of available or ready (e.g., sterilized or clean and in not in need of repair or maintenance, proper location, etc.) resources 110 to perform the procedures on the patients 115. Step 415 can include acquiring preferences of the stakeholders (e.g., resources 110 or patients 115).

Step 420 can include assigning or allocating or reserving the available blocks or slots of time in the schedule of the resources 110 or patients 115 according to the forecast durations calculated by the duration module 120 to perform the delivery of healthcare to the patients 115. The scheduling module 400 can allocate or re-allocate the blocks of time in the series of schedules in such a way as to simultaneously satisfy preferences of one or more of the stakeholders (e.g., resources 110 or patients 115).

The embodiment of the scheduling module 400 can adjust, change or re-sort allocation of the blocks or slots of time at any instant dependent on incoming current data acquired from resources 110 or patients 115. An example of a tracked event or data that can cause adjustment of the schedule of the resources 110 includes an unavailability of the resource 110 (e.g., personnel or equipment) that can be caused by various upstream or downstream events, including: delay in cleaning, delay in procedure, unable to perform or receive patients, malfunctions in personnel (e.g., illness) or equipment, unplanned locations of personnel or equipment, inadequate inputs from clinical or administrative systems, adequacy of patient health status not within specification, addition of unscheduled procedures, and unscheduled drops of procedures. Changes in assumption in one or more of the activities can also cause the system 100 to adjust the schedule of resources 110 in delivery of healthcare to the patients 115.

An embodiment of the scheduling module 400 can simulate effects to or changes to the performance of the schedule according to alternative plans and contingencies. An embodiment of the schedule module 400 is generally configured to operate similar to a forward-looking trouble-shooter or "radar" of the schedule process. The scheduling module 400 can combine the schedule of resources 110 with location and information of the state of the resources 110, creating a display that identifies when deviations of the schedule of forecast durations occur, a cause of the deviation, an illustration of interdependencies of one or more procedures with other procedures, and can calculate or simulate changes to the schedule as a result of alternative decisions. Thereby, this embodiment of the scheduling module 400 can receive instructions from the stakeholders in response to the display of "what is" occurring, "what is" likely to occur in combination with calculated risk or probability output by the system 100, and recommended changes such that schedule risk can be minimized in proceeding forward.

Step 425 can include identifying or prospectively assessing or predicting one or more interdependencies in the schedule of the resources 110. For example, the system 100 can identify resources 110 (e.g., a medical equipment, surgeon, staff, consumables, etc.) to perform a procedure on an admitted patient 115. Assume the location and availability of one or more resources 110 conflicts with the schedule. In response, the system 100 can create an alarm at the user interface 130 as a warning for action. The system 100 can continuously monitor or track the acquired information as the time of need approaches for the resource 110 in the scheduled performance of the procedure, and can locate other interdependent allocations of blocks of time for the resources looking forward or later in the schedule. If one or more interdependencies be unknown, the scheduling module 400 can automatically calculate or identify interdependencies or confirm candidate interdependencies according to input (e.g., potential limited availability of one or more resources 110, potential surge in number of patients 115 at a certain time period or overall for a day, etc.) in the simulation of a 'what-if' scenario in the schedule of resources 110.

Other examples of resources 110 that can be part of the critical path of interdependency with forecast start times, duration or completion times or interdependency with other resources 110 or interdependency with patients 115 can include: detecting a nurse calling in to indicate absence or tardiness from an upcoming shift, detecting a surgical case cart that may not be correctly inventoried, or detecting a cleaning technician occupying one room after the predicted completion time in view of another room requiring clean up by a predicted start time. The system 100 can calculate a ripple effect of these above-described example variations and interdependencies and can change the schedule of resources 110 to minimize delays and minimize schedule risk, where the changes can include adjusting the forecast start times, adjusting the forecast duration, adjusting the forecast completion time, suggesting added resources 105, or adjusting the forecast locations of the resources 110 to minimize the risk in the revised schedule of resources 110 in delivery of healthcare service to the patients 115.

An example of how the disclosed method 400 can be applied to dynamically respond to a change, assume a patient's vital biometric readings 212 are not within surgical protocol specifications prior to the administration of anesthesia or in any care protocol of interest. Surgery (and Surgeon) commencement can be dependent upon numerous resources 105 (e.g., anesthesiologist and anesthesiology delivery equipment). In this example, delivery of anesthesia by the anesthesiologist and equipment can be dependent upon, inter alia, a biological readiness of the patient 115 to receive the forthcoming procedure(s). An embodiment the system 100 can manage interdependencies in such a way that the appropriate factors can be given action (e.g., re-scheduling other resources 105 of same function) if those factors left unmanaged or along current trend increase a likelihood of delay in the schedule start or duration of procedure or diminish objectives of the institution (e.g., patient satisfaction, capacity, low infection rates, costs, revenue, resource utilization, rate of return (ROI), etc.). In this example, biometrical readings acquired from the patient 115 can be outside a threshold to be ready for a surgical procedure. This factor may delay a time of delivery of anesthesiology to the patient 115, which may delay a time of surgeon to scrub in before performing the surgical procedure and re-schedule that surgeon and other prerequisites for the surgical procedure. This is an example of factors of interdependencies of biometric readings of the patient 115, pre-procedure tasks, and resources 110 (e.g., equipment, space, personnel) and a given forecast duration that defines the schedule of resources 110 to deliver healthcare to patients 115. An embodiment of step 430 can include allocating or re-allocating the reservation of the blocks or slots of time in the schedule of the resources 110 so as to increase or maximize the confidence of the schedule, or alternatively to lower or minimize the risk of the schedule.

The totality of schedule confidence and risk may not be a summation of individual duration probability distributions. Rather, because of the many parallel paths, some of which have interdependencies, a critical path's duration can create a forecast duration time that can be compared to a schedule in order to calculate the difference between schedule and prediction. Replications can be run to statistically sample from the task duration estimates, and in each replication the critical path can be recalculated. Thereby, the system 100 can calculate the overall risk or confidence or probability. Individual sub-tasks may or may not impact the critical path, yet the sub-tasks may have dependency on other tasks. For these reasons, an embodiment of the method 400 can include combining a Monte Carlo simulation technique with the critical path method technique. An alternative analytical embodiment of the method 400 can include applying a closed form analytical technique, and analytically describing the task duration probability density functions relative to the critical path.

An embodiment of the user interface 130 can generally illustrate (e.g., graphic, audio, etc.) the schedule of resources 110, risk to the schedule of resources, opportunities and constraints to the schedule of resources 110, variation to the schedule of resources 110, miscellaneous activities or states (e.g., cleaning, service, etc.) of the schedule resources 110, and the above-described acquired tracked data or input for use in directing procedures in the delivery of healthcare to patients 115. The user interface 130 can also output an alarm representative of an alert to a problem.

An example of the user interface 130 can include a patient kiosk or workstation that can gather input information for later use to reduce variation, and operable to interact with the stakeholders (e.g., resources 110 or patients 115). Another example of the user interface 130 can include a printed document or a display output at the patient kiosk or workstation or mobile platform such as a personal digital assistant (PDA). Kiosk screens may be displayed with schedule, planning and/or decision support information or alerts, for example. The provided information can be targeted, compliant and relevant to the stakeholder. The user interface 130 can include a graphic whiteboard or multiple computer terminals (e.g., Microsoft Windows-based and/or green screen computers) or flat panel screens hung on the wall to illustrate or visualize output of the system 100 in different rooms. The user interface 130 can include color to show whether or not operations are proceeding according to schedule. In certain embodiments, user interface 130 can include a graphic illustration of in a window pane format that can pop up to overly an application running graphics on a display screen.

Figure 5:
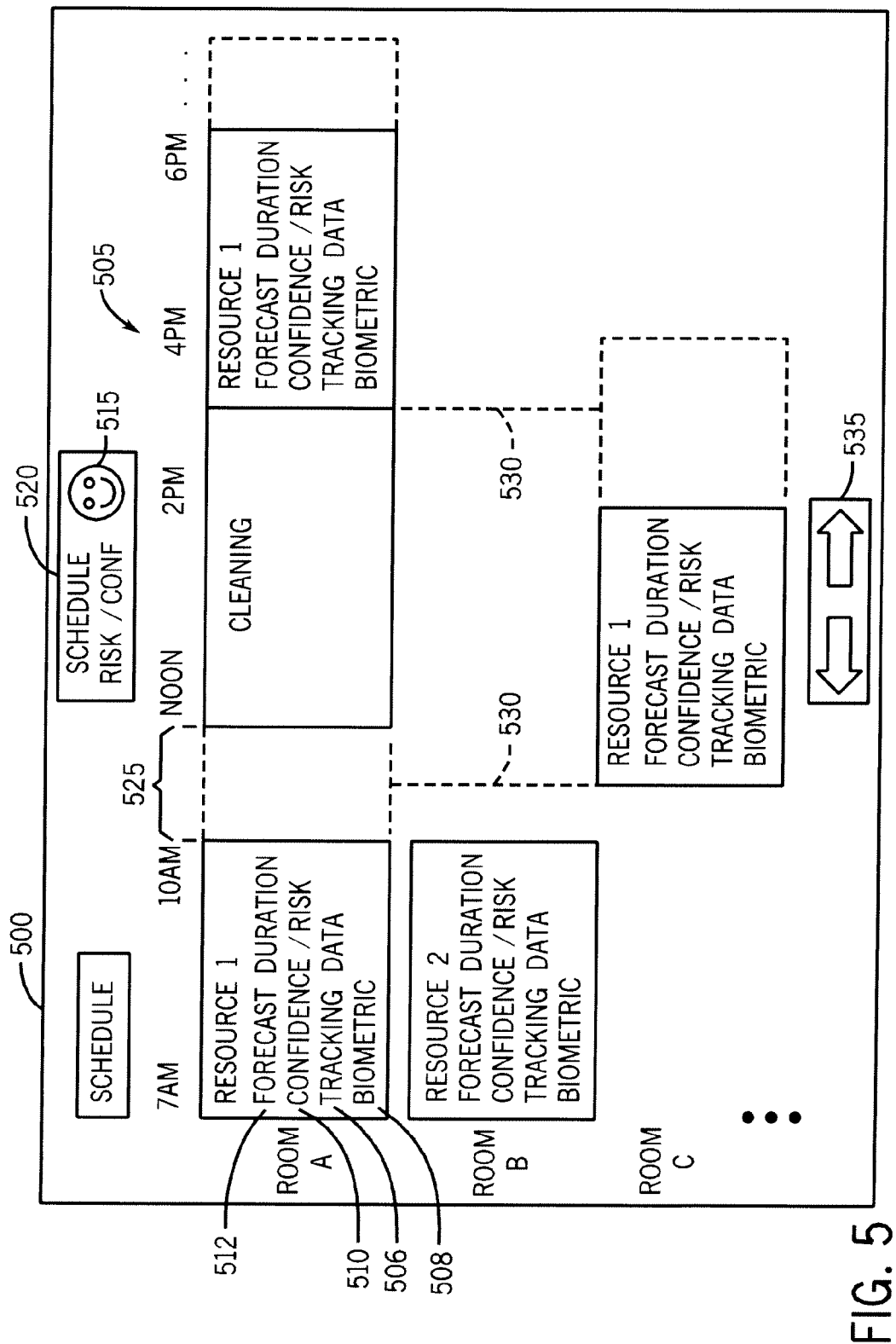
FIG. 5 is a schematic diagram that shows an embodiment of a user interface of the system of FIG. 1.

FIG. 5 is a schematic diagram that illustrates an embodiment of the user interface 500, similar to the user interface 130 of FIG. 1. The user interface 500 can generally show a graphic illustration 505 schedule of the resources 110 (e.g., rooms, equipment, staff, etc.), including data of tracked utilization or consumption 506 of resources 110 in a manner to enhance illustration of a state of dynamic interdependencies between scheduling of resources 110, tracked biometric data 508 of the patients 115, and can illustrate automatic adjustments or instructions to manually intervene in the scheduling of the resources 110.

An embodiment of the output shown in the user interface 500 can include an illustration or graphic representation 510 of the schedule risk or confidence or probability of completion of one or more tasks or individual schedule procedures within the forecast durations 512. Examples of the output can include a color indicator (e.g., red/yellow/green) and/or a graphic illustration 515 of a happy or sad face representative of the schedule risk or probability of completion relative to a threshold that can enhance rapid review by the user so readily identify portions of the schedule 505 to manually intervene or utilize the "what-if" decision support functionality of the system 100 and method 400 relative to the schedule 505.

The user interface 500 can also illustrate output of the likelihood or confidence or risk 520 that the overall candidate schedule 505 will be met. The user interface 130 can also display graphic illustrations 525 directed to candidate resources 110 or blocks of time of the candidate schedule 505 (e.g., forecast durations) or patients 115 that the system 100 identifies as candidate causes of a potential variance or causes a forecast of a low confidence in the schedule 505, in combination with a graphic illustration 530 of the identified potential interdependencies to other resources 110 or patients 115 or blocks of time in the schedule.

Still referring to FIG. 5, the user interface 500 can illustrate or generate alarm, action and/or warning if the tracked actual duration or forecast risk exceeds the threshold variation, if the procedure does not begin at the forecast start clock time and or actually end by the forecast end clock time or within a threshold thereof according to the candidate schedule of resources 110. The user interface 530 can also illustrate output of candidate schedules in response to input directed to represent simulated conditions or events.

The output generated by the system 100 via the user interface 500 can further include deterministic or probabilistic data or a combination thereof. For example, the deterministic data can include a state transition (such as a patient's biometric trend relative to a protocol exceeding a clinical guide and the patient's status or state can be changed to one with new process implications that will impact the scheduled block of time of one or more resources 110). An example of the output of the probabilistic data can include transition of a graphic illustration one probability to another (e.g., triggering, for example, transition from a happy face to a sad face) in response to detecting a delay or exceeding a schedule block of time of one resource 110 that includes an interdependency that may increase the schedule or decrease the probability of completion of the schedule block of time of another resource 110 or readiness of the same resource 110 at a later schedule allotment of time.

The interface 500 can include graphic tool or illustration 535 that when actuated can cause an advance or scroll forward in time or back in history through the illustration of the allocated blocks of times that comprise the schedule of resources 110 in delivery of healthcare. For example, the scroll or advance tool 535 can advance through the schedule blocks of time of the resources 110 prior to the start of a shift by adjusting the virtual time (e.g., via a slider bar or dial) and watching the schedule unfold in combination with a illustration of the relative risks of delays or early completions associated with the respective forecast duration of the procedures. Thereby, the scroll tool 535 can illustrate sensitivities and key risks to the schedule and alarms when scheduled risks or probability of completion exceed or drop below thresholds. Movement or shifting of the scroll tool 535 (e.g., mouse, graphic illustration of scroll bar, adjusting virtual time via a slider bar or dial, etc.) in one direction can cause scrolling forward in time through the illustration of the forecast schedule of resources 110, and shifting of the scroll tool 535 in another direction can cause advancement in virtual time through an illustration or replay of historical data or actual events (e.g., recorded start or completion times) of the schedule of resources 110.

Accordingly, the scroll tool 535 of the user interface 130 can illustrate the unfolding of the schedule of the resources 110 along with the respective risks or probability of delays or early completions. The edges of the displayed task duration may also be adjusted by interaction with the graphic illustrations such as a mouse click or screen touch by the input device. The corresponding numerics can be updated for analytical purposes. In response to actuation of the scroll tool 535, the system 100 can also automatically calculate a change in probability or confidence or risk with the change in value of the forecast duration.

The scroll tool 535 can also virtually advance through historical blocks of schedule of resources 110 over a past day or several days or any variant of time so as to illustrate or analyze "what-was" illustration of the workflow dynamics that can be used to derive training, activity costs, billing, verification of procedural protocol. The user interface 500 can further output one or more of the above-described illustrations in combination with electronic medical records (EMR), healthcare information systems (HIS) to/from data, data acquired by status/tracking/monitoring systems 540 (e.g., radio frequency identification (RFID) tracking system, optical recognition for shape of medical equipment/instrument/consumables/operating room activity, etc.), medical device data (e.g., electrocardiogram (EKG), anesthesiology, etc.), manual observations entered via input to the user interface 130, and availability of the stakeholders (e.g., resources 110 or patients 115).

Figure 6:
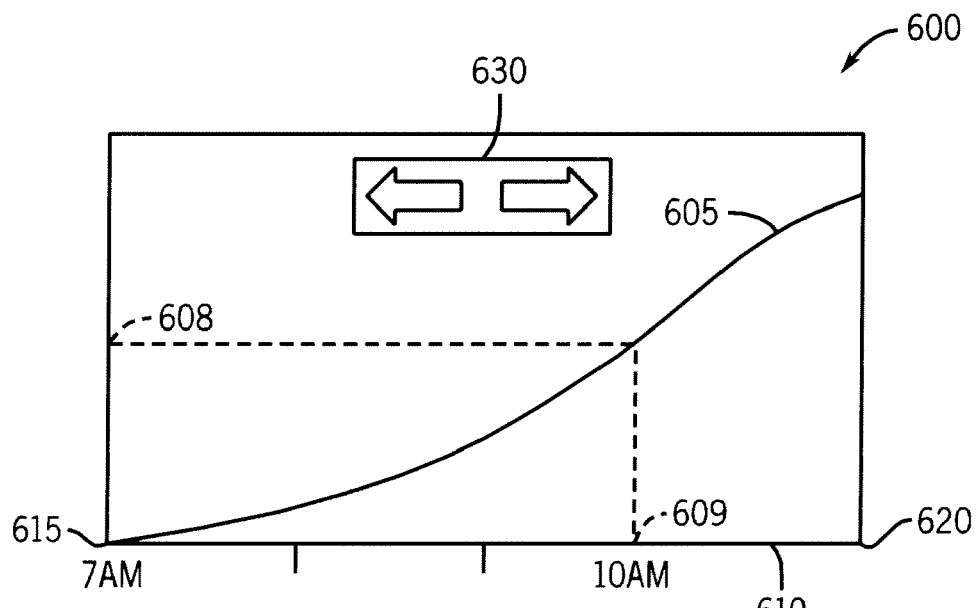
FIG. 6 is a schematic illustration of another example of a user interface of the system of FIG. 1 that can be directed to mitigate schedule risk.

Referring to FIG. 6, an example of the user interface 600 can include a combination of a graphic illustration 605 of the CPDF 320 graphically integrated or conceptually superimposed to show changes in forecast probability or confidence or risk 608 overlaying or integrated or compared relative to the task's graphical illustrations 610. This may be for blocks of time 609 reserved in the schedule of resources 110 or tasks within blocks of time 609. Thereby, the user interface 600 can enhance understanding of the probabilities of delays or early finishing activity so that bottlenecks or underutilized resources can be dealt with before the delay or underutilized capacity becomes a lost opportunity for throughput or care quality. As such, the system 100 can output a probability that one or tasks of a protocol will begin per a scheduled start or end time. The system 100 can change the probability in the schedule of resources, and can change the baseline start time or start time of any task in the protocol or associated schedule of resources, in response to acquiring (e.g., via the input or predetermined) a desired confidence interval in the forecast schedule of resources.

Alternatively, the system 100 can acquire a desired probability of completion of the schedule of resources, and the probabilities or confidence intervals for each task of the protocol of resources can be back-propagated such that a contribution of the risk level of each task can be analyzed relative to its impact on the sensitivity to the completion of the schedule of resources. According to another embodiment, the system 100 can acquire a desired probability or confidence in any given task of the protocol or schedule of resources, and the system 100 can calculate the downstream and upstream the probabilities or confidence in downstream or upstream interdependencies to other scheduled protocol of tasks or resources. Any acquired setting can be generally aligned at zero probability of forecast duration or scheduled time 615, or one hundred-percent probability or confidence of a start time 620 or completion time, or any number in between for the schedule of resources 110 and tasks.

Figure 7:
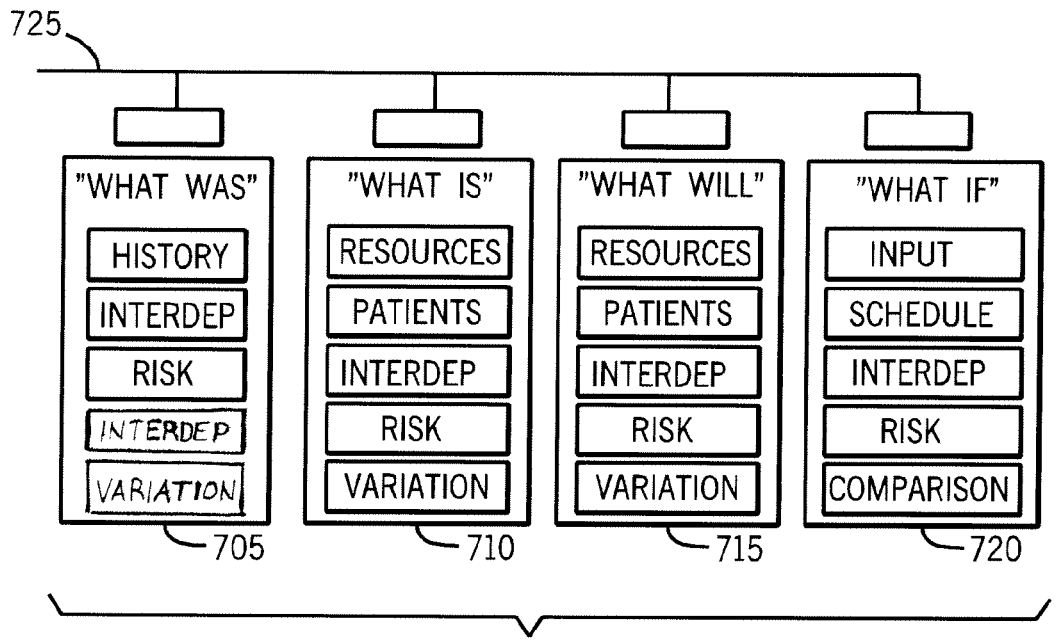
FIG. 7 shows a schematic diagram of yet another embodiment of a user interface of the system of FIG. 1 that can illustrate a temporal process context of the institution.

Referring to FIG. 7, an example of the user interface 130 (see FIG. 1) can include an illustration of output from the system 100 that includes a series of dynamic views or displays 705, 710, 715 and 720 of the overall schedule for multiple patients 115 or on a per patient basis that can be generally classified as the following: "what-was", "what is", "what will-be", and/or "what if", respectively, that may be in combination with graphic representations 725 of a 'satisfactory' state, a 'warning' (e.g., request to execute a pre-emptive action), a 'danger' (e.g., alarm to indicate variation to the candidate schedule), a change in biometrical state of the patient 115 an recognitions and illustration of a recommended care protocol, or similar thereto. The titles and types of the above-described views can vary.

An embodiment of the "what-was" view 705 can includes a history of activities, interdependences and risk levels. An embodiment of the "what-is" view 710 can include an illustration of current information collected in regard to the resources 110 or patients 115 at the time of being viewed, such as interdependences, states, acquired data, and current calculated risk to schedule. The "what-is" view 710 can also include an illustration of current deployment and use of resources in response to the tracked state or use or consumption of resources or in view of tracked data of the patient's biometrical state relative to a protocol or threshold. An embodiment of the "what will-be" view 715 can include predicted or trend information (e.g., risk or confidence, interdependencies, availability/readiness of resources 110 or patients 115, variation from forecast duration, etc.) a future time period. The above-described views 705, 710, 715 or 720 can be illustrated as a series of frames or panes in a WINDOWS™ format for display on a screen. An embodiment of the input data of the tracked data of the patient's biometrical state can be acquired from an electronic medical record, data acquired via various methods of tracking (e.g., optical tracking, RFID tracking, inference from other instruments or clinical data, etc.), or messaging, etc.

The "what-if" view 720 can include predicted information or risk or variation to the schedule of the resources 110 or patients 115 in view of a simulated set of input parameters or assumptions (e.g., representative of strategy to change, resource availability, unforeseen delays or failures, etc.) for comparison relative to one of the above views (e.g., "what was" view 850). An embodiment of the "what if" view 720 can include illustration of the comparison to the "what is" view 710 that can notify stakeholders (e.g., resources 110 or patients 115, etc.) of the affected resources 110 in response to a change in tracking data of one or more of the resources 110 or patients 115. The "what if" view 720 can further include illustration of the output of the change to the forecast risk or probability of completion of the current schedule of resources 110 relative to a threshold or objective.

A technical effect of the above-described output of the system 100 enables the operator to view sensitivities and key risks to one or more portions of the schedule of resources 110 and to view alarms when scheduled risks or probability of completion exceed or drop below thresholds. Another technical effect of the above-described views output by the system 100 to the user interface 130 can enhance scheduling of resources 110 that may directly or indirectly affect variation and throughput, wait times, or capacity of the institution to deliver healthcare to the patients 115.

Figure 8:
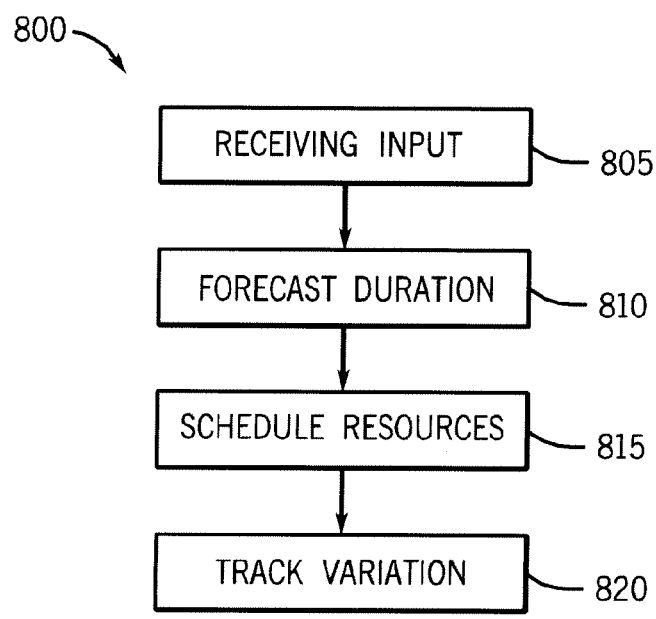
FIG. 8 illustrates a flow diagram illustrative of another embodiment of method to deliver healthcare to a patient.

FIG. 8 illustrates an embodiment of a method 800 to deliver healthcare to a patient in accordance with the subject matter described herein. The embodiment of the method 800 includes a step 805 of calculating a schedule block(s) of time allotted for each of the resources 110 to perform the tasks in delivering healthcare to the series of admitted patients 115. The method 800 can be represented as program instructions for execution by one or more processors of the system 100. Step 805 includes receiving input data or acquiring historical data of the list of resources 110 to execute a protocol of a procedure to deliver healthcare to the patients 115. Step 810 includes calculating a forecast duration to complete the tasks or procedures of the protocol designated for each of the patients 115.

Step 815 can include calculating the schedule of resources 110 to deliver healthcare to the series of patients 115, including scheduled resources 110 (e.g., surgeon, staff, medical equipment, room or space, etc.) to be available for a start time and end time, at the desired or forecast place or location of occurrence of the task that are consuming the scheduled time of the resources 110 per the protocol. An embodiment of step 815 can include populating a list and categorization of resource names/identifications with a count of available resources 110, and identifying those resources 110 connected to executing the protocol for the procedure. Where a threshold number of resources 110 called for to execute the protocol exceeds the count of available resources 110, the system 100 can output a warning or alarm representative of the condition or event. Also, the system 100 may identify and generate an alarm in response to detecting a count of schedule resources 110 to execute the tasks or procedures of the protocol exceeds the historical or precedent or threshold counts of resources 110 to execute the tasks or procedures of the protocol.

Step 815 can include acquiring or receiving a set of decision support rules that can be generally represented by program instructions for the processors of the system 100 to execute to automatically change or adjust the scheduling of the resources 110 in response to detecting or tracking variation in acquired data of the scheduled resources 110 or the patients 115. For example, assume that a surgical case cart should include a specialized surgical tool such as sterilized probe to perform a procedure. If the system 100 detects that the schedule sterilized probe may not be available, the system 100 can automatically search for and identity other sterilized probes scheduled on standby to be available. If there are constraints that cannot be solved, the system 100 via the what-if view 720 can automatically simulate other schedules of resources to find a candidate schedule within a predetermined or acquired range of probability or confidence of completion. The decision support rules can be example-based, evidential reasoning based, fuzzy logic-based, case-based, and/or other artificial intelligence-based, for example.

Step 815 can include automatically tracking or receiving input of additions and deletions in workload, and re-calculate the availability in scheduling of resources 110 accordingly to meet the change in workload. Examples can include a request to add an emergency surgery, a staff person calls in sick, etc. Each resource 110 can be identified having a state or status generally representative of a relevant degree to which the resource 110 can be available in delivering healthcare at a point in time. As an example, the system 100 may identify that available resources 110 (e.g., medical equipment) in delivering healthcare in the scheduled procedure should be designated or identified to have a state of or being in calibration and sterilization thirty minutes before the surgical procedure is to begin. The embodiment of the system 100 can continuously or periodically track and assess the state of each of the resources 110.

Continuing the example described above, assume the resource 110 (e.g., surgeon, x-ray imaging system) can be scheduled to deliver healthcare for a surgery procedure in the operating room. The step 815 can include generating or outputting a Boolean indicator representative of whether resource 110 is or is not in location, or a likelihood of being in the designated location in a future time. For example, assume the resource 110 can scheduled to be in an operating room for a surgical procedure beginning in one hour. However, the resource 110 (e.g., surgeon, x-ray imaging system, etc.) may be undergoing sterilization or cleaning. The system 100 can calculate and output a forecast duration to the user interface 130 to illustrate forecast completion or attain a status of sterilization or clean deemed sufficient for transport to the scheduled operating room within the hour.

Step 820 can include tracking or monitoring the actual location of patients and resources 110 versus the scheduled time and place for availability and location of resources 110 or patients 115 relative to forecast durations and locations of procedures and resources 110 to deliver healthcare. For example, the step 820 can include acquiring biometric or status code data of the patient from resources 110, for example, stationary or ambulatory clinical apparatus, devices and equipment such as an oxygen reading from a pulse oximeters, electrocardiogram (EKG), an infrared (IR) or radio frequency (RF) device or tag, or an anesthesia delivery device 110, etc. The system 100 can integrate measurements or tracking of the biometrical data of the patient 115 to assess progress relative to the tasks of the protocol and the forecast durations thereof. Dependent on this biometrical data, the system 100 can calculate a likelihood or risk that a scheduled tasks or procedures of the protocol and schedule resources 110 associated therewith will complete within the forecast duration.

In response to detecting the risk or likelihood of completion of the schedule of resources 110 or tasks of the protocol exceeds a threshold, the system 110 can output information representative of relationships and interdependencies of resources 110 that can be cause increased risk in the scheduling of other protocols and the metric of schedule risk. The simulation and heuristic capability of the system 100 can have a technical effect of an ability to test feasibility and robustness of the schedule of resources 110 or protocol compared to overall objectives.

The system 110 can further include a set of decision support rules that can be generally represented by program instructions for the processors of the system 100 to execute to resolve interdependencies in the variation of resources 110, or to reduce change of risk or confidence associated with interdependencies to variation of resources 110. The system 100 can execute one or more of the decision support rules to identify or calculate a strategy(s) to identify or calculate changes (e.g., add resources 110, drop resources 110, change locations of resources 110, etc.) to the schedule of resources 110 with interdependencies so as to reduce changes to the risk or confidence or probable duration in the candidate schedule of resources 110. Statuses or states of resources (e.g., assets, personnel, equipment, rooms, etc.) can be monitored periodically or continuously. In many instances, the objective is to lower clinical risk as well as schedule risk and the system can execute commands to readjust the schedule for clinical risk reduction. For example, the system 100 can output the known correlation between having one or two staff scheduled for a task or procedure relative to reduction in risk or likelihood of completion of the schedule of resources 110 or protocol on time (e.g., scheduling two staff can outweigh the task time and resource consumption so as to achieve a desired or greater level of safety).

Figure 9:
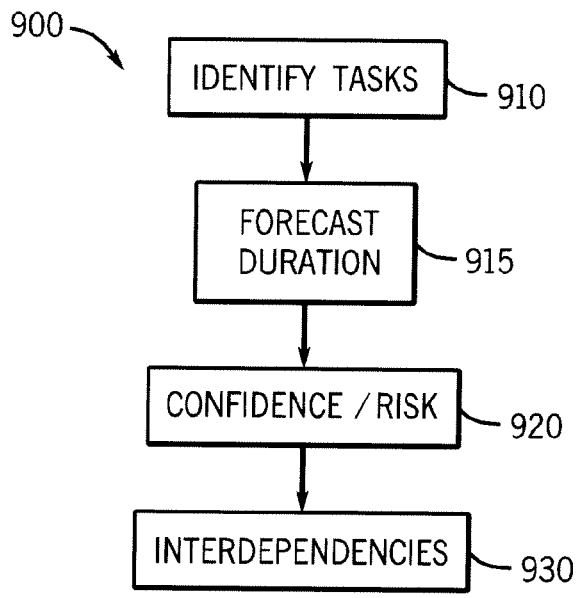
FIG. 9 shows a flow diagram illustrative of yet another method of scheduling resources in delivery of healthcare to patients.

FIG. 9 illustrates an embodiment of a method 900 to manage schedules of resources 110 in delivering healthcare. An embodiment of step 910 includes identifying task(s) and resource(s) 100 of a procedure (e.g., surgical or clinical procedure, etc.) involved in delivering the healthcare to the patients 115. An embodiment of step 915 includes calculating the forecast duration of each procedure or one or more multiple tasks that comprise an individual procedure, and allocating or assigning or reserving blocks or slots of time and location of the resources 110 according to the forecast duration of each task or procedure in the delivery of healthcare. In response to input or request to deliver healthcare to the patient 115, the system 100 can identify the resources 110 to deliver the healthcare, track the availability (e.g., location, readiness, other reservation of use, etc.) of the resources 110 to deliver the healthcare, and can allocate the beginning and ending times to reserve the resources 110 according to the forecast duration so as to deliver the healthcare to the patient 115.

Step 920 includes calculating the likelihood or schedule confidence or schedule risk of those forecast beginning and completion times of location and use of the resources 110 actually occurring. Step 920 can include calculating an integration of adjustment factors to the above-described schedule risk representative of the reliability of the resources 110 (e.g., tardiness of staff, attendance record of staff, malfunctioning equipment, etc.). Step 920 can also include calculating factors representative of the degree of robustness or risk or confidence of the schedule of resources 110 in response to tracked parameters including availability or readiness of resources 110, likelihood or probability of exogenous variation to the schedule (e.g., likelihood of adds or drops to the schedule of the resources 110), or forecast of volatility of the schedule of resources 110 in response to adjustment factors representative of parameters such as seasonal variation in case load, variation in capacity, etc.

The method 900 can further include a step 930 of identifying one or more the resources 110 that define a critical path of interdependency of scheduled allotments or slots of time having an increased likelihood of causing additional delay or bottleneck in delivering healthcare to the patients relative to other resources 110 in response to a variation from the forecast start time, forecast duration, or forecast completion time. The system 100 can continuously or periodically monitor metrics of the resources 110 identified as the critical path. An example of the metrics can include: an availability, readiness (e.g., sterile), or state (e.g., cleaning, repair, use) of the resource 110. An embodiment of the step 930 of identifying resources 110 of the critical path can include calculating a weighted parametric mathematical algorithm including: exceeding a threshold or having a highest number of independencies relative to other resources 110, or exceeding a threshold or having a highest risk of unavailability relative to other resources 110, etc.

Figure 10:
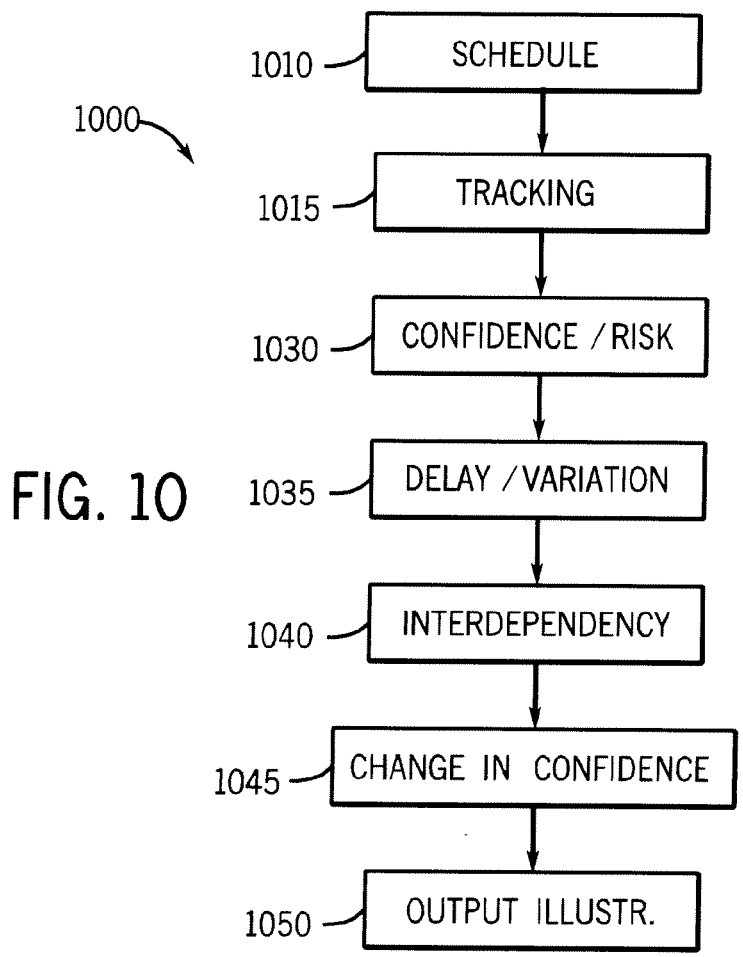
FIG. 10 illustrates a flow diagram that shows yet another embodiment of a method to schedule resources in delivery of healthcare to patients.

FIG. 10 illustrates an exemplary embodiment of a method 1000 to schedule resources 110 according to the subject matter of this application pertaining to mutual exclusivity of being in multiple concurrent tasks and locations. Assume that the resources 110 include multiple operating rooms and other facilities that share a pool or fleet of resources 110. Assume examples of resources 110 in a critical path as described above can include a doctor that may be available for a surgery in only one room at an instant of time, an emergency department, or one or more rooms that, at a given time, may be behind schedule or exceed the forecasted duration or completion time. Also assume that a series of patients 115 arrive through the emergency department of the hospital to receive emergency or scheduled services. Also assume the resources 110 include a hospital preoperative department.

Step 1010 can include calculating a schedule of resources 110 to deliver healthcare to the patient 115. The step 1010 of calculating the schedule can occur before arrival of the patient 115 or after arrival of the patient 115 to the institution. The system 100 can create the schedule of resources 110 in response to the request of delivery of services such as surgery to the patient 115 according to a preference of the surgeon to schedule certain blocks of time in a day or day of the week to perform the surgical procedure, or vice versa, in view of allocated blocks of time that the surgeon desires to be not available to perform surgery procedures (e.g., reserved office time, rounds, out of town, vacation, etc.). The system 100 can output the schedule of resources 110 immediately or in minutes, hours, days, weeks or months in advance of the actual procedure.

Step 1015 can includes receiving or tracking preparatory information (e.g., above-described biometric data of the patient 115) prior to the forecast start time of the procedure in accordance to the schedule of resources 110. Examples of preparatory information can include tracking a location of the patient 115 in the surgical preparation area, tracking requisite completion of and signature on release or insurance forms, or tracking biometric information including a blood pressure, a heart rate, a blood chemistry, other lab data, and a digestive chemistries of the patient 115 within a protocol or threshold to receive permission to proceed to the surgical procedure.

Assume for sake of example that the system 100 creates a schedule of the resource 110 that includes allocating the resource 110 to be at a first operating room 1120 in 15 minutes prior to the performance of a first surgical procedure on a first patient, and allocating the same resource 110 to locate at a second operating room in one hour in performance of a second surgical procedure.

Step 1030 includes calculating a probability or risk or confidence that the resource 110 will be available or ready by the schedule allotment of time at the first operating room to deliver the first surgical procedures with the respect to the first patient, and a probability that the resource 110 will be available or ready by the schedule allotment of time at the second operation room to deliver the surgical procedure to the second patient. For sake of example, assume the system 100 calculates a 65% probability that the first operating room will be available or ready within 45 minutes, the system 100 calculates an 80% probability that the first operating room will be available within 50 minutes, and a 98% probability that the first operating room will be available within 70 minutes. Furthermore, for sake of example, assume the system 100 calculates the scheduling of the surgeon to perform both the first surgical procedure at the first operating room on the first patient, and also schedules the surgeon with a start time in one hour at the second operating room to perform the scheduled procedure on the second patient.

Assume the first patient delays in signing the release form. Step 1035 includes detecting the delay or variation (e.g., exceeds a threshold of time) to the forecasted duration to receive the signature of the first patient on the release form required before performing the first surgical procedure. Step 1040 includes identifying an interdependency of the delay in the start time of performance of the resource 110 in performing the first surgical procedure, and how the interdependency lies along an identified critical path that can then lead to a delay in performance of the second surgical procedure at the second operating room at the scheduled allotment of start time. In response to detecting the delay in receiving the signed release form, the system 100 also identifies that the availability of the surgeon to perform the first surgical procedure also comprises the critical path that can lead to delay in performance of the second surgical procedure at the second operating room at the second allotment of time.

Step 1045 includes calculating the change in probabilities of completion of the start time and end times of the schedule of resources 110 or protocol of tasks in response to the delay in receiving the signed form from the first patient. For example, assume the system 100 calculates a schedule risk of 35%, that the first surgery would otherwise start on time relative to the predicted scheduled start time, that variation (e.g., threshold delay) from the predicted start time of the first surgical procedure will occur if the signed form is not received with a first time threshold. The system 100 can calculate a risk or likelihood or probability of 65% that the predicted second start time of the resource 110 for the second surgical procedure will occur if the signed form is not received with the first time threshold, according to an algorithm that represents the scheduling of the resource 110 (e.g., the surgeon) as part of the critical path of interdependency with the scheduling of the resource 110 for the second start time for the second surgical procedure at the second operating room. To compare the difference between scheduling resources 110 along critical path versus non-critical path related tasks, suppose for example that the release form for the first surgery was not required to start and that there was no delay in the predicted start time of the surgical procedure. Assuming other prerequisites were met, there would be no delay in schedule of the resource 110 for the second surgical procedure at the second location, and no change in the probability of the predicted start time of the second surgical procedure.

Step 1050 can include outputting an illustration of a first alert (yellow graphic illustration) at the user interface 130 illustrative of the change in the schedule risk associated with not receiving the signed form from the first patient by the threshold time that in combination with the scheduling of the surgeon comprises the critical path of interdependency to increase the schedule risk relative to the predicted start time of the first and second surgical procedures. The step 1050 can further include outputting a second illustration of a second alert (red graphic illustration) at the user interface 130 in response to detecting that the signed form may not be received from the first patient after a second threshold time period or scheduled risk level in view of identified critical path of the interdependency of the resource 110 relative to the second start time of the second surgical procedure to the second patient.

The system 100 can continue to track and adjust the schedule of the resource 110 if called for as the resource 110 moves between locations (e.g., the first and second operating rooms) or changes state of readiness (e.g., dirty to clean, unsterile to sterile) in view of the forecast start times and forecast completion times as output in the schedule of the resources 110.

Once detecting delivery of the surgical procedure(s), the user interface 130 can include an illustration as part of the schedule of resources 110 that is representative of instructions to move location or an illustration of movement of the patients to a post-operative (post-op) recovery area. The system 100 can update the availability status or state of the surgeon or other resource 110 (e.g., operating room, staff, imaging system), and track transition of the resources 110 from unsterile or dirty status to ready or clean status, or movement of the resources 110 from tracked locations relative to the forecast location. The system 100 can also calculate predicted times to move the patients from the post-operative recovery area, predicted times of floor beds to receive the patients, or predicted time to discharge patients from the institution, for example. These above-described steps can be repeated or continue until the patient is discharged from the institution.

The system 100 can identify or track the availability of the resources 110 such as floor beds as part of the critical path of interdependency with the discharge of the patients 115 from the institution. In response to detecting delay in the availability of the floor beds relative to the forecast start time of bed availability or actual versus forecast duration of completion of tasks leading to discharge, the system 100 can generate alerts to be output to the interface 130 directed to resources 110 required in the workflow. In addition, the interdependencies related to admissions, etc can be updated with changes associated with discharge of the patients.

Figure 11:
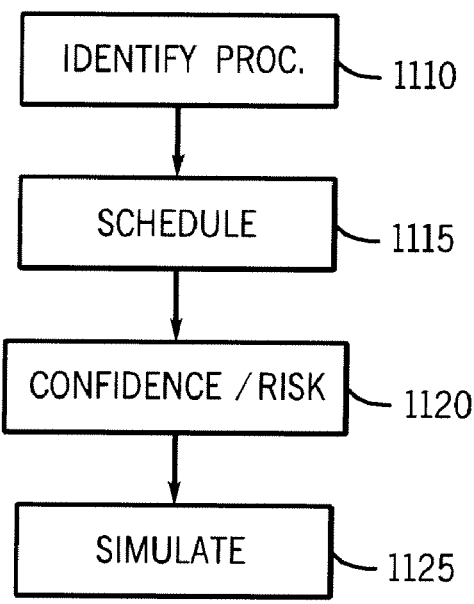
FIG. 11 illustrates a flow diagram of yet another embodiment of a method to manage delivery of healthcare to a series of patients that can be from a risk management perspective.

FIG. 11 illustrates another embodiment of a method 1100 to manage delivery of healthcare with a series of resources 110 to a series of patients 115. Step 1110 can includes identifying procedures to deliver healthcare to treat the series of patients 115. Step 1115 can include calculating the schedule of resources 110 according to calculation of forecast durations to perform the procedures with the resources 110. Step 1120 can include calculating or predicting the risk to completion of predicted start or completion times with respect to one or more of the tasks that comprise the procedures of the protocol of healthcare delivery to the patient, relative to one or more overall procedures, or relative to the overall the schedule of the resources 110. As described above, the step 1120 can include generating a PDF in accordance to stored or received data (e.g., historical durations of procedures, peer recommendations of procedure durations, generally accepted standards, etc.), and integrating the PDF into a CPDF that generally expressions the probability of less than a threshold variation from the forecast duration.

Step 1125 can include simulating task durations, or simulating the scheduling of resources 110 or patients 115 in response to assumptions or forecast values of one or more of the above-described parameters for illustration, similar to the "what-if view" described above. Examples of models that the system can use to simulate or forecast the task durations or schedules of the resources 110 to deliver healthcare to the patients 115 in view of assumptions input to the system include: an agent based simulation model, a discrete event simulation model, a continuous or system dynamic simulation model, a Monte Carlo simulation model, or a critical path calculation model or combination thereof or comparison of results generated by the above models. An embodiment of the models can generate predictions or forecasts directed to the tasks, some of which can become critical path depending upon the simulation replications of tasks and schedules. From simulation replications of tasks and schedules, the system can calculated predicted start and completion times of the schedule of resources 110. Numerical methods can also be employed independently or in combination with simulation techniques to output forecast schedule of resources 110, and the risk or confidence therein of completion.

For example, assume the system 100 calculates or predicts a first forecast duration of a first procedure based on historical information (e.g., mode, medium, etc.) with a sixty percent probability of no threshold variation, and calculates a likelihood or probability of ninety-five percent that there will be no threshold variation from a second forecast duration that exceeds the first forecast duration. The system 100 can calculates that the first forecast duration of the planned surgical procedure completes earlier than predicted nearly 50% of the occurrences, and a delay occurs in nearly 50% of the occurrences. The system 100 can calculate that a delay to one or more of the scheduled resources 110 can be part of the critical path of interdependency relative to an impact in delaying other surgical procedures, staff, or that can adversely impact an increase in wait time of other patients 115.

For example, an embodiment of the method 1100 can include calculating the schedule of the resources via a discrete event simulation algorithm. An embodiment of the discrete event simulation algorithm generally includes an ordered step-through of determined procedures or tasks in discrete time increments. At each time step, the system 100 can identify or calculate the resources 110 performing in the task(s) at hand. Should concurrent tasks involve the same resource(s) 110, the method 1100 can include calculating a priority for each task, calculating an order of priority of the tasks, and outputting the schedule of the resources 110 to serve multiple tasks in a generally simultaneous time frame in a manner that is not mutually exclusive.

The above-described embodiment of the method 1100 can be configured with path independent assumptions and linear or formulaic correlations that assume simulated tasks are much the same as the historical assumptions. The embodiment of the method 1100 can include calculating the schedule of resources dependent on historical assumptions and from discrete events in ordered tasks and the logical call of the resources. The above-described embodiment of the method 1100 can include performing an agent-based simulation 1220 that assumes a prioritization rule for the set of resources 110 in generating the schedule of resources 110 in response to the surrounding environment or events.

Method 1100 can include continuous or periodic or dynamic (e.g., in response to threshold change in tracked parameter) simulation in view of tracking of parameters described above that can affect the scheduling of resources 110 and further including the following: movement of resources 110, improvement in staff skill in view of exposure to mix of different cases or exposure to frequent procedures, "burnout" or loss of skill in view of infrequent exposure to procedures or lack of training, staff turnover, reputation in delivery of healthcare, capacity to delivery healthcare, or financial operating margin, or combination thereof as acquired via acquired data questionnaires, surveys, etc. of resources 110 (e.g., staff) of patients 115 or peers in other independent institutions.

Figure 12:
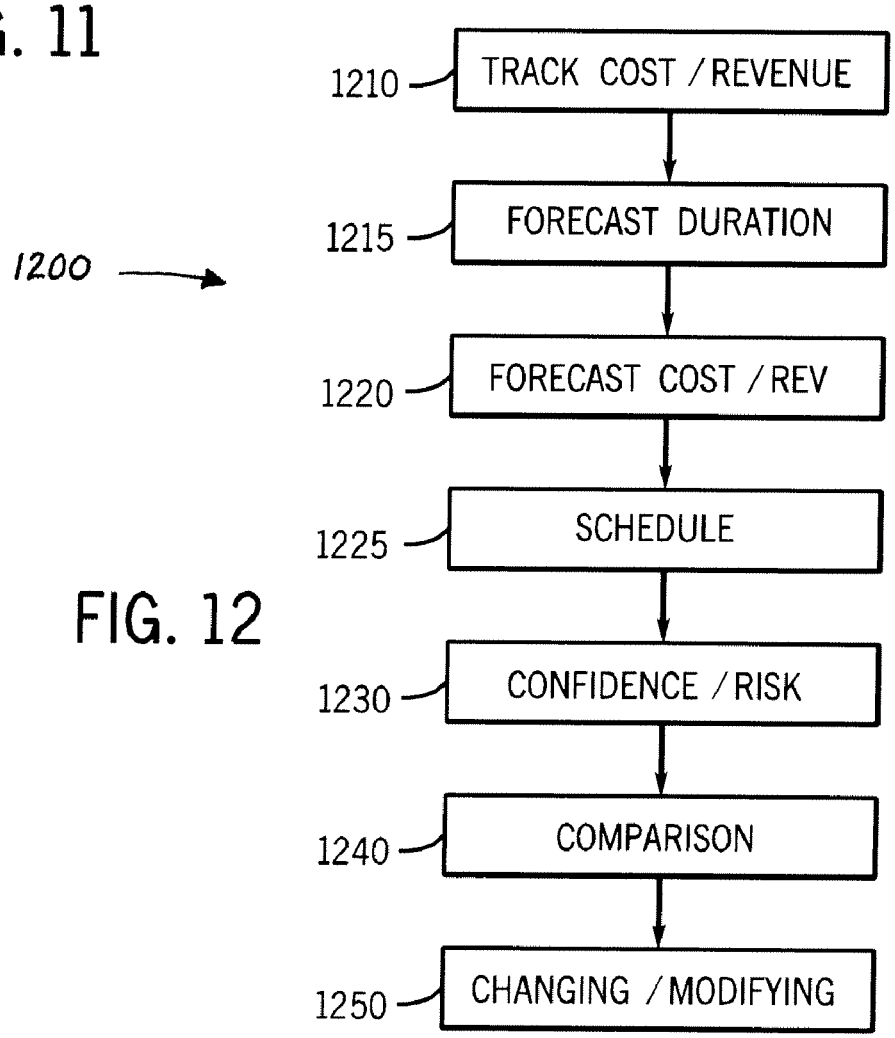
FIG. 12 shows a flow diagram of an embodiment of a method to manage delivery of healthcare in view of economic parameters.

FIG. 12 illustrates an embodiment of a method 1200 to schedule the series of resources 110 in the delivery of healthcare to patients 115 in view of economic parameters.

Step 1210 includes tracking costs or revenue on per time basis or per procedure basis associated with the resources 110 delivery of healthcare to the series of patients 115. The tracking of costs or revenue can be in view of a break-even point of financial loss in the delivery of healthcare. Tracking can include acquiring codes representative of reimbursement of healthcare costs by an insurer, cost of resources 110 (e.g., tasks or procedures eligible for reimbursement, salary or overtime pay to staff, rental or lease of medical equipment, cost directed to use of surgical suite or clinical space, etc.).

Step 1210 can include tracking a change in operating margin or capacity in view of various tracked economic parameters, including: costs associated with investment in additional or replacement resources 110 (e.g., capitalized equipment, consumable stock, physical plant, staffing levels, training of staff, recruiting staff, etc.), attraction or drop-off in admission of patients 115 to receive delivery of healthcare relative to threshold, or an ability to meet one or more financial targets relative to threshold. Attracting more entrants than the capacity of the system 100 can increase risk in the availability or performance of resources 110, such as associated with staff burnout or poor process outcomes.

Step 1215 includes calculating the forecast duration per procedure to delivery healthcare to the patients 115. Step 1220 includes calculating the forecast cost relative to revenue per procedure to deliver healthcare to the patients 115. Step 1225 includes calculating the schedule of resources that maximizes revenue, operating margin, or otherwise generally equates forecast revenue in view of costs (e.g., financial break even point) to deliver healthcare to the patients 115. Step 1230 can include calculating the probability of or risk in depleting the operating margin or falling below the break-even point or other comparison of revenue to costs, or probability or risk in sustaining the operating margin or sustaining above the break-even point of revenue over costs. Step 1230 can include generating a PDF that expresses the comparison of acquired data (e.g., historical, outside provider, acquired from peer institutions, etc.) of number executions of procedures relative to sustenance above or below operating margin, or duration of procedures in view sustenance above or below operating margin, etc. Step 1230 can further include integrating the PDF into a CPDF that generally defines the probability of sustaining above or below the operating margin for a procedure.

Step 1240 can include comparing the likelihood or probability of sustaining the operating margin or other forecast economic parameter (e.g., overtime cost, non-value added time, total cost, etc.) relative to a threshold. Step 1250 can include changing/modifying the schedule of the resources 110 (e.g., an imaging system, a surgeon, staff, etc.) in view of or in response to the comparison of step 1240. The technical effect of the method 1200 includes increasing an ability of stakeholders to make more informative strategic economic decisions in view of probabilistic trade-offs.

In another example, the system 100 can adjust output of the schedule of resources 110 in response to a change in health risk (e.g., a stroke to a patient) as received via the user interface 130 or as tracked by the system 100. The change to the schedule can include automatically modifying the scheduled or allocation of blocks of time of one or more resources 110 (e.g., an imaging system such as a magnetic resonance imaging (MRI) system) to acquire images of the heightened risk patient, delaying the predicted start or duration of predicted time to acquire images of a lower risk or less critical patients. or having a lowest overall risk of completion of the modified schedule or that will result in a greatest tracked level of staff or overall resource 110 (e.g., staff) or patient satisfaction (e.g., least wait time, overall patient satisfaction, etc.).

The above-description is directed to delivery of healthcare services for example only. Detailed descriptions of hospital locations and services are for example only, are applicable to other departments in the hospital, an ambulatory clinic, doctor's office or ward set up on a temporary basis such as for emergency or conflict, one or multiple institutions, and work environments outside of healthcare.

One or more elements or constructions of one or more embodiments of the subject matter described above may be combined with one or more elements or constructions of other embodiments of the subject matter described above and is not limiting on the subject matter described herein.

In a healthcare delivery environment (e.g., hospital, healthcare clinic, urgent care facility, etc.) involving numerous interdependencies to deliver healthcare to patients, variation in any interdependent factor may cause changes to made to the schedule to deliver service to the patient. A technical effect of the system and method described herein facilitate understanding and proactive management of factors that, if otherwise ignored or allowed to accelerate, will likely increase a probability of delay and preclude one or more process operating objectives from being met. A review of an upcoming period's process task, schedule risks and contingency plans is beneficial to provide a contextual understanding of activities as well as to solicit opinions of staff to then modify the schedule for improvement.

Another technical effect of the above-described system and method can reduce variation in delivery of healthcare to patients several ways by providing capabilities that include: (1) to reduce internal (endogenous) variation from interdependency variation that can be anticipated and subsequently; (2) to incorporate variation into the process planning and control as far forward into the time line such that not only more accurate averages can be used in scheduling; (3) to combine information flows as to the status of staff, patients, equipment and facilities with the scheduled plan such that anticipatory alerts can be provided when schedule risk crosses a threshold as well as a diagnosis as to the cause of the likely or actual source of the deviation that is sufficient and actionable for staff to intervene and resolve or revise the schedule of resources; and, (4) to understand and incorporate the effects of external (exogenous) variation resulting from difficult to forecast events, such as surges, medical reason procedure delay, equipment failure and staff sickness.

Yet another technical effect of the above-described subject matter includes providing a system and a method to manage changes to a schedule to accommodate changes that are internally or externally induced—and to do so in a way that minimizes overall health delivery system throughput or quality degradation. Specific assets such as plant & equipment, people, physical location and information are exemplary entities being tracked and dynamically managed. The above-described system and method can automatically organize tasks and assets of a process to more effectively achieve immediate and longer-term macro objectives. In certain embodiments, scheduled tasks are organized using, for example, a critical path method (CPM) and the tasks there-in are exposed to durations which are probabilistic and are either within the endogenous variation control of the system or are exogenous factors to which the system must be robust to. Measures of duration, availability and reliability to calculate an enumeration of scenarios in the context of variation can be used to determine the probabilities of meeting a selected schedule (schedule risk). The probabilistic measures of duration, availability and reliability can be functions of path dependent consumption and utilization decisions that are made to determine the use of the assets of the process. Using a multi-modality simulation methodology, for example, a process transfer function of the probabilistic measures may be derived. The prediction of duration, both endogenous and exogenous, that are described by simulation to schedule the resources and the logic of the tracked interdependencies can be used to calculate schedule risk in the CPM method.

Embodiments of the system and method described can also simulate schedules calculated in response to potential events (e.g., natural disasters, or where desired to improve performance under past conditions) to train of personnel or improve preparedness. At any point, the system and method can simulate the changes to the schedule of tasks and resources in response to the potential event. For example, the system and method can calculate the schedule of handover of patients at shift changes of the personnel in response to potential events. In another example, the system and method can in general real-time calculate a change to the predetermined schedule of resources in response to occurrence of unexpected events (e.g., delay or acceleration in deliver of a surgical procedure or execution of a diagnostic examination, change in current place or state of a resource, and the chain of interdependencies that can be impacted). The system and method can identify causes and effects of the identified variations and calculate the changes in the scheduling of resources to minimize a loss of performance (e.g., delay time) in delivering quality healthcare to the patient.

Embodiments of the subject matter are described in the general context of method steps which may be implemented in one embodiment by a program product including machine-executable instructions, such as program code, for example in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represents examples of corresponding acts for implementing the functions described in such steps.

Embodiments within the scope of the present subject matter can include articles of manufacture or products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the subject matter described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the subject matter may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

The foregoing description of embodiments has been presented for purposes of illustration and description. It is not intended to be exhaustive or to limit the subject matter to the precise form disclosed, and modifications and variations are possible in light of the above teachings or may be acquired from practice of the subject matter. The embodiments were chosen and described in order to explain the principals of the subject matter and its practical application to enable one skilled in the art to utilize the subject matter in various embodiments and with various modifications as are suited to the particular use contemplated.

We claim:

1. A method to schedule a plurality of resources in delivery of healthcare to a plurality of patients, the method comprising the steps of:

identifying an availability of one or more of the resources to deliver the healthcare to each of the plurality of patients; and through execution of instructions by at least one processor of at least one machine:

calculating a predicted duration to deliver the healthcare to each of the patients;

calculating a schedule including at least one block of time dependent on the predicted duration for at least one of the plurality of resources to deliver healthcare to one or more of the patients, the at least one block of time including a start time and an end time;

calculating a confidence level in the schedule, the confidence level including at least one of a probability that the at least one resource will not be available for the at least one block of time of the schedule or a likelihood that the at least one resource will be available for the at least one block of time in the schedule; wherein the step of calculating the confidence includes creating a cumulative probability density function generated from historical data of availability of one or more of the plurality of resources in delivery of healthcare and accumulating the composite effects of durations of previous tasks in the schedule in a causal relationship captured in a constraints based relationship; and outputting the schedule and the confidence level in the schedule.

2. The method of claim 1, the method further comprising receiving a desired range of confidence for a particular task, appointment time, resource use, or patient time, the schedule including one or more of specific scheduled appointments or resource utilizations, wherein the step of calculating the schedule includes generating the schedule having the confidence level within the desired range of confidence for one or more resources identified in the schedule in a manual or automatic scenario testing framework.

3. The method of claim 1, wherein the step of outputting the schedule and the confidence level includes outputting a first schedule and a first confidence level in the first schedule dependent on a current data of the plurality of the resources, and outputting a second schedule and a second confidence level in the second schedule dependent on a change to the first schedule, the second schedule based on an explicit causal relationship of a variance on one scheduled activity to another as a function of the resources requisite to enable a scheduled activity to start or end.

4. The method of claim 1, wherein the confidence level is in one of the start time of the at least one block of time or in the end time of the at least one block of time.

5. The method of claim 1, the method further comprising the step of identifying at least one block of time of scheduling of the plurality of resources as a critical path of the schedule, the step of identifying the critical path dependent on one or more of a number of interdependencies of the scheduling of the at least one resource with other resources of the at least one resource, or dependent on the confidence level of the at least one resource being available for at least one block of time in the schedule of the plurality of the resources.

6. The method of claim 1, wherein the at least one resource includes one of the group comprising a physician, a clinician, a technician, a nurse, an imaging system, a wheel chair, a bed, a room, and a department in a care facility.

7. The method of claim 1, wherein the step of outputting the display includes outputting graphic representations representative of confidence level in one or more blocks of time of the schedule of the plurality of the resources.

8. The method of claim 1, the method further comprising the step of tracking a biometric data of the patient, wherein the step of calculating the confidence level in the schedule depends on the biometric data, the biometric data is selected from the group of parameters comprising a blood pressure reading, a pulse, a respiratory rate, an electrocardiogram data, or a consciousness.

9. The method of claim 1, comprising steps of:
calculating a probability that a healthcare delivery event in the schedule will start by a scheduled time;
tracking progress of an additional healthcare delivery event scheduled for an earlier time than the healthcare delivery event, wherein tracking progress of the additional healthcare delivery event includes monitoring at least one resource or patient associated with both the healthcare delivery event and the additional healthcare delivery event; and
based on the tracking of progress of the additional healthcare delivery event and on dependency of the healthcare delivery event and the additional healthcare delivery event on the at least one resource or patient associated with both the healthcare delivery event and the additional healthcare delivery event, calculating an updated probability that the healthcare delivery event will start by the scheduled time.

10. A method to schedule a plurality of resources in delivery of healthcare to a plurality of patients, the method comprising the steps of:
identifying an availability of one or more of the resources to deliver the healthcare to each of the plurality of patients;
calculating a predicted duration to deliver the healthcare to each of the patients;
calculating a schedule including at least one block of time dependent on the predicted duration for at least one of the plurality of resources to deliver healthcare to one or more of the patients, the at least one block of time including a start time and an end time;
calculating a confidence level in the schedule, the confidence level including at least one of a probability that the at least one resource will not be available for the at least one block of time of the schedule or a likelihood that the at least one resource will be available for the at least one block of time in the schedule; wherein the step of calculating the confidence includes creating a cumulative probability density function generated from historical data of availability of one or more of the plurality of resources in delivery of healthcare and accumulating the composite effects of durations of previous tasks in the schedule in a causal relationship captured in a constraints based relationship;
outputting the schedule and the confidence level in the schedule; and
tracking a location of one or more of the plurality of resources or at least one of the plurality of patients via an optical tracking system operable to perform computer-aided recognition of an acquired digital image of the one or more of the plurality of resources.

11. An article of manufacture comprising:
at least one machine readable medium; and
a plurality of computer readable instructions stored on the at least one machine readable medium for execution by a processor, the plurality of computer readable instructions representative of the following steps:
identifying an availability of one or more of a plurality of resources to deliver healthcare to each of a plurality of patients,
calculating a predicted duration to deliver the healthcare to each of the patients,
calculating a schedule including at least one block of time dependent on the predicted duration for each the plurality of resources to deliver the healthcare to one or more of the patients, the at least one block of time including a start time and an end time,
calculating a confidence level in the schedule, the confidence level including at least one of a probability that at least one of the resources will not be available for the at least one block of time of the schedule or a likelihood that at least one of the resources will be available for the at least one block of time in the schedule; wherein the step of calculating the confidence includes creating a cumulative probability density function generated from historical data of availability of one or more of the plurality of resources in delivery of healthcare and accumulating the composite effects of durations of previous tasks in the schedule in a causal relationship captured in a constraints based relationship; and
outputting the schedule and the confidence level in the schedule.

12. The article of manufacture of claim 11, the plurality of computer readable instructions further representative of the steps of receiving a desired range of confidence, wherein the step of calculating the schedule includes generating the schedule having the confidence level within the desired range of confidence.

13. The article of manufacture of claim 11, wherein the step of outputting the schedule and the confidence level includes outputting a first schedule and a first confidence level in the first schedule dependent on a current data of the plurality of the resources, and outputting a second schedule and a second confidence level in the second schedule dependent on a change to the first schedule.

14. The article of manufacture of claim 11, wherein the confidence level is in one of the start time of the at least one block of time or in the end time of the at least one block of time.

15. The article of manufacture of claim 11, the plurality of computer readable instructions further representative of the step of identifying at least one block of time of scheduling of the plurality of resources as a critical path of the schedule, the step of identifying the critical path dependent on one or more of a number of interdependencies of the scheduling of the at least one resource with other resources of the at least one resource, or dependent on the confidence level of the at least one resource being available for at least one block of time in the schedule of the plurality of the resources.

16. The article of manufacture of claim 11, wherein the step of outputting the display includes outputting graphic representations representative of confidence level in one or more blocks of time of the schedule of the plurality of the resources.

17. The article of manufacture of claim 11, the plurality of computer readable instructions further representative of the steps of receiving a biometric data of the patient, wherein the step of calculating the confidence level in the schedule depends on the biometric data, the biometric data is selected from the group of parameters comprising a blood pressure reading, a pulse, a respiratory rate, an electrocardiogram data, a measure of activity, chemical sensing, image-derived measures, or a consciousness of the at least one patient.

18. The article of manufacture of claim 11, wherein the plurality of computer readable instructions include instructions representative of:

calculating a probability that a healthcare delivery event in the schedule will start by a scheduled time;

tracking progress of an additional healthcare delivery event scheduled for an earlier time than the healthcare delivery event, wherein tracking progress of the additional healthcare delivery event includes monitoring at least one resource or patient associated with both the healthcare delivery event and the additional healthcare delivery event; and based on the tracking of progress of the additional healthcare delivery event and on dependency of the healthcare delivery event and the additional healthcare delivery event on the at least one resource or patient associated with both the healthcare delivery event and the additional healthcare delivery event, calculating an updated probability that the healthcare delivery event will start by the scheduled time.

* * * * *